(12) United States Patent
Sokolowski

(10) Patent No.: US 10,806,943 B2
(45) Date of Patent: Oct. 20, 2020

(54) DEVICE FOR REPETITIVE NERVE STIMULATION IN ORDER TO BREAK DOWN FAT TISSUE MEANS OF INDUCTIVE MAGNETIC FIELDS

(71) Applicant: BTL Medical Technologies S.R.O., Prague (CZ)

(72) Inventor: Tobias Sokolowski, Pullach im Isartal (DE)

(73) Assignee: BTL Medical Technologies S.R.O., Prague (CZ)

( * ) Notice: Subject to any disclaimer, the term of this patent is extended or adjusted under 35 U.S.C. 154(b) by 0 days.

(21) Appl. No.: 16/415,927

(22) Filed: May 17, 2019

(65) Prior Publication Data
US 2019/0336783 A1 Nov. 7, 2019

Related U.S. Application Data

(63) Continuation of application No. 14/412,875, filed as application No. PCT/IB2013/001896 on Jul. 2, 2013.

(30) Foreign Application Priority Data

Jul. 5, 2012 (DE) .................... 10 2012 013 534

(51) Int. Cl.
*A61N 2/02* (2006.01)
*A61N 2/00* (2006.01)
*A61N 1/40* (2006.01)

(52) U.S. Cl.
CPC ................. *A61N 2/02* (2013.01); *A61N 1/40* (2013.01); *A61N 2/006* (2013.01)

(58) Field of Classification Search
CPC ............. A61N 1/40; A61N 2/006; A61N 2/02
See application file for complete search history.

(56) References Cited

U.S. PATENT DOCUMENTS

| 3,658,051 A | 4/1972 | MacLean |
| 3,915,151 A | 10/1975 | Kraus et al. |
| 4,237,898 A | 12/1980 | Whalley |
| 4,454,883 A | 6/1984 | Fellus |
| 4,456,001 A | 6/1984 | Pescatore |
| 4,674,505 A | 6/1987 | Pauli et al. |

(Continued)

FOREIGN PATENT DOCUMENTS

| CN | 201906360 U | 7/2011 |
| DE | 1118902 B | 12/1961 |

(Continued)

OTHER PUBLICATIONS

Abulhasan, J.F., et al., "Peripheral Electrical and Magnetic Stimulation to Augment Resistance Training," Journal of Functional Morphology and Kinesiology, 1(3):328-342, (Sep. 2016).

(Continued)

*Primary Examiner* — Christine H Matthews
(74) *Attorney, Agent, or Firm* — Sterne, Kessler, Goldstein & Fox P.L.L.C.

(57) ABSTRACT

A device for repetitive nerve stimulation for development of muscle using inductive magnetic fields, having a stimulation coil replaceably attached to a stand and accommodated in a plastic housing, and a pulse generator for electrically actuating the stimulation coil.

29 Claims, 8 Drawing Sheets

(56) References Cited

U.S. PATENT DOCUMENTS

| | | | |
|---|---|---|---|
| 4,850,959 A | 7/1989 | Findl | |
| 5,067,940 A | 11/1991 | Liboff et al. | |
| 5,718,662 A | 2/1998 | Jalinous | |
| 5,766,124 A | 6/1998 | Polson | |
| 5,782,743 A | 7/1998 | Russell | |
| 5,807,232 A | 9/1998 | Espinoza et al. | |
| 5,984,854 A | 11/1999 | Ishikawa et al. | |
| 6,063,108 A | 5/2000 | Salansky et al. | |
| 6,086,525 A | 7/2000 | Davey et al. | |
| 6,099,459 A * | 8/2000 | Jacobson | A61N 2/02 128/897 |
| 6,117,066 A | 9/2000 | Abrams et al. | |
| 6,179,770 B1 | 1/2001 | Mould | |
| 6,213,933 B1 | 4/2001 | Lin | |
| 6,402,678 B1 | 6/2002 | Fischell et al. | |
| 6,418,345 B1 | 7/2002 | Tepper et al. | |
| 6,527,694 B1 | 3/2003 | Ishikawa et al. | |
| 7,520,849 B1 | 4/2009 | Simon | |
| 7,608,035 B2 | 10/2009 | Farone | |
| 7,744,523 B2 | 6/2010 | Epstein | |
| 7,946,973 B2 | 5/2011 | Peterchev | |
| 7,998,053 B2 | 8/2011 | Aho | |
| 8,979,727 B2 | 3/2015 | Ron et al. | |
| 9,586,057 B2 | 3/2017 | Ladman et al. | |
| 9,636,519 B2 | 5/2017 | Ladman et al. | |
| 9,919,161 B2 | 3/2018 | Schwarz et al. | |
| 9,937,358 B2 | 4/2018 | Schwarz et al. | |
| 10,124,187 B2 | 11/2018 | Schwarz et al. | |
| 10,245,439 B1 | 4/2019 | Schwarz et al. | |
| 2001/0031906 A1 | 10/2001 | Ishikawa et al. | |
| 2003/0050527 A1 | 3/2003 | Fox et al. | |
| 2003/0158585 A1 | 8/2003 | Burnett | |
| 2006/0152301 A1 | 7/2006 | Rohwedder | |
| 2006/0187607 A1 | 8/2006 | Mo | |
| 2006/0287566 A1 * | 12/2006 | Zangen | A61N 2/02 600/15 |
| 2007/0083237 A1 | 4/2007 | Teruel | |
| 2008/0249350 A1 | 10/2008 | Marchitto et al. | |
| 2008/0306325 A1 | 12/2008 | Burnett et al. | |
| 2008/0306326 A1 | 12/2008 | Epstein | |
| 2009/0018384 A1 | 1/2009 | Boyden et al. | |
| 2009/0108969 A1 | 4/2009 | Sims et al. | |
| 2010/0036368 A1 | 2/2010 | England et al. | |
| 2010/0081971 A1 | 4/2010 | Allison | |
| 2010/0087699 A1 | 4/2010 | Peterchev | |
| 2010/0121131 A1 | 5/2010 | Mathes | |
| 2010/0152522 A1 | 6/2010 | Roth et al. | |
| 2010/0160712 A1 | 6/2010 | Burnett et al. | |
| 2010/0179372 A1 | 7/2010 | Glassman | |
| 2010/0222629 A1 | 9/2010 | Burnett et al. | |
| 2010/0309689 A1 | 12/2010 | Coulson | |
| 2010/0331603 A1 | 12/2010 | Szecsi | |
| 2011/0021863 A1 | 1/2011 | Burnett et al. | |
| 2011/0077451 A1 | 3/2011 | Marchitto et al. | |
| 2011/0130618 A1 | 6/2011 | Ron et al. | |
| 2012/0053449 A1 | 3/2012 | Moses et al. | |
| 2012/0172653 A1 | 7/2012 | Chornenky et al. | |
| 2012/0302821 A1 | 11/2012 | Burnett | |
| 2012/0310033 A1 | 12/2012 | Muntermann | |
| 2013/0030239 A1 | 1/2013 | Weyh et al. | |
| 2013/0053620 A1 | 2/2013 | Susedik et al. | |
| 2013/0123568 A1 | 5/2013 | Hamilton et al. | |
| 2013/0123764 A1 | 5/2013 | Zarsky et al. | |
| 2013/0123765 A1 | 5/2013 | Zarsky et al. | |
| 2013/0137918 A1 | 5/2013 | Phillips et al. | |
| 2013/0150653 A1 | 6/2013 | Borsody | |
| 2013/0331637 A1 | 12/2013 | Greff | |
| 2014/0148870 A1 | 5/2014 | Burnett | |
| 2014/0330067 A1 | 11/2014 | Jordan | |
| 2014/0371515 A1 | 12/2014 | John | |
| 2015/0025299 A1 | 1/2015 | Ron et al. | |
| 2015/0123661 A1 | 5/2015 | Yui et al. | |
| 2015/0133717 A1 | 5/2015 | Ghiron et al. | |
| 2015/0157873 A1 * | 6/2015 | Sokolowski | A61N 2/006 600/14 |
| 2015/0216719 A1 | 8/2015 | Debenedictis et al. | |
| 2015/0328475 A1 | 11/2015 | Kim et al. | |
| 2015/0367141 A1 | 12/2015 | Goetz et al. | |
| 2016/0030763 A1 | 2/2016 | Midorikawa et al. | |
| 2016/0250494 A1 | 9/2016 | Sakaki et al. | |
| 2017/0001024 A1 | 1/2017 | Prouza | |
| 2017/0001025 A1 | 1/2017 | Schwarz et al. | |
| 2017/0001029 A1 | 1/2017 | Pribula et al. | |
| 2017/0001030 A1 | 1/2017 | Pribula et al. | |
| 2017/0072212 A1 | 3/2017 | Ladman et al. | |
| 2017/0106201 A1 | 4/2017 | Schwarz et al. | |
| 2017/0120067 A1 | 5/2017 | Prouza | |
| 2018/0001106 A1 | 1/2018 | Schwarz | |
| 2018/0125416 A1 | 5/2018 | Schwarz et al. | |
| 2018/0236254 A1 | 8/2018 | Schwarz et al. | |

FOREIGN PATENT DOCUMENTS

| | | |
|---|---|---|
| DE | 3205048 A1 | 8/1983 |
| DE | 3610474 A | 10/1986 |
| EP | 0459401 A1 | 12/1991 |
| JP | 2017518857 A | 7/2017 |
| WO | 03/103769 A1 | 12/2003 |
| WO | WO-2015179571 A1 | 11/2015 |

OTHER PUBLICATIONS

Bachasson, D., et al., "Quadriceps Function Assessment Using an Incremental Test and Magnetic Neurostimulation: a Reliability Study," Journal of Electromyography and Kinesiology, 23(3):649-658, Elsevier, England, (Jun. 2013).

Barker, A.T, "An Introduction to the Basic Principles of Magnetic Nerve Stimulation," Journal of Clinical Neurophysiology, 8(1):26-37, Lippincott Williams & Wilkins, United States, (Jan. 1991).

Basic Protocol of Salus, Talent with Incontinence Chair, REMED, 1 page.

Behrens, M., et al., "Repetitive Peripheral Magnetic Stimulation (15 Hz RPMS) of the Human Soleus Muscle did not Affect Spinal Excitability," Journal of Sports Science and Medicine, 10(1):39-44, Dept. of Sports Medicine, Medical Faculty of Uludag University, Turkey (Mar. 2011).

Beilin, G., et al., "Electromagnetic Fields Applied to the Reduction of Abdominal Obesity," Journal of Cosmetic & Laser Therapy, 14(1):24-42, Informa Healthcare, England, (Feb. 2012).

Bustamante, V., et al., "Muscle Training With Repetitive Magnetic Stimulation of the Quadriceps in Severe COPD Patients," Respiratory Medicine, 104(2):237-245, Elsevier, England, (Feb. 2010).

Bustamante, V., et al., "Redox Balance Following Magnetic Stimulation Training in the Quadriceps of Patients With Severe COPD," Free Radical Research, 42(11-12):939-948, Informa Healthcare, England, (Nov. 2008).

Caress, J.B., et al., "A Novel Method of Inducing Muscle Cramps Using Repetitive Magnetic Stimulation," Muscle Nerve, 23(1):126-128, John Wiley & Sons, United States, (Jan. 2000).

Clinical Application of Electro Magnetic Stimulation, Salus-Talent, Korea Society of interventional Muscle and Soft Tissue Stimulation Therapy, CR Technology, 141 pages.

Course in Physical Therapy, Presentation, Jan. 4, 2013, 156 pages.

CR Technology, Salus-Talent, Technical File of Electro-magnetic Stimulator, Document No. TF-005, 2008, 241 pages.

CR Technology, Technology for Health and Business for Human Being, investor relations, 2008, 21 pages.

Effective PEMF Magnetic Fat Reduction Slimming Body Beauty Salon Machine (PEMF Star), Wolfbeauty 1980, PEMF STAR, China, Retrieved from the Internet: (URL: https://www.ec21.com/product-details/Effective-PEMF-Magnetic-Fat-Reduction--8928746. html), 2019, 5 pages.

FMS Tesla Stym—AKCE, Medila Cenova nabidika, Price offer c. 191, 24 pages.

Goetz, S.M., et al., "Coil Design for Neuromuscular Magnetic Stimulation Based on a Detailed 3-D Thigh Model," IEEE Transactions on Magnetics, 50(6):10, IEEE, (Jun. 2014).

(56) References Cited

OTHER PUBLICATIONS

Gorodnichev, R.M., "Magnetic Stimulation of Muscles as New Method to Enhance Their Strength," Velikie Luki State Academy of Physical Culture and Sport, Velikie Luki, 2016, 5 pages.

Hamnegard, C.H., et al., "Quadriceps Strength Assessed by Magnetic Stimulation of the Femoral Nerve in Normal Subjects," Clinical Physiology and Functional Imaging, 24(5):276-280, Blackwell, England, (Sep. 2004).

Han, T.R., et al., "Magnetic Stimulation of the Quadriceps Femoris Muscle: Comparison of Pain With Electrical Stimulation," American Journal of Physical Medicine & Rehabilitation, 85(7):593-599, Lippincott Williams & Wilkins, United States, (Jul. 2006).

Hasala, O., et al., Case Study of Treating Acute Ankle Distortion Using TMS, Charles University, Faculty of Physical Education and Sports, Prague, Czech Republic, 4 Pages.

Increasing Physiotherapy Presence in Cosmetology, Spa Inspirations, Jan. 2012, pp. 34-35.

Iskra Medical, Magneto System, 2012, 2 pages.

Katuscakova, Z.L., et al., High Induction Magnet Therapy in Rehabilitation, Department of Physiactric Rehabilitation, 2012, 72 pages.

Lampropoulou, S.I., et al., "Magnetic Versus Electrical Stimulation in the Interpolation Twitch Technique of Elbow Flexors," Journal of Sports Science and Medicine, 11(4):709-718, Dept. of Sports Medicine, Medical Faculty of Uludag University, Turkey (Dec. 2012).

Lin, V.W., et al., "Functional Magnetic Stimulation for Restoring Cough in Patients With Tetraplegia," Archives of Physical Medicine and Rehabilitation, 79(5):517-522, W.B. Saunders, United States, (May 1998).

Lin, V.W., et al., "Functional Magnetic Stimulation of Expiratory Muscles: a Noninvasive and New Method for Restoring Cough," Journal of Applied Physiology (1985), 84(4):1144-1150, American Physiological Society, United States, (Apr. 1998).

Madariaga, V.B., et al., "[Magnetic Stimulation of the Quadriceps: Analysis of 2 Stimulators Used for Diagnostic and Therapeutic Applications]," Archivos De Bronconeumología, 43(7):411-417, Elsevier Espana, Spain, (Jul. 2007).

MAG and MORE Gmbh, Magnetic and Life Science System, Power Mag, 12 Pages.

Mag Venture, Magnetic Stimulation, Accessories Catalogue, Accessories Catalogue, 2011, 54 pages.

MagVenture, MagPro® by MagVenture®, Versatility in Magnetic Stimulation, World Leading Transcranial Magnetic Stimulation Systems, 2011, 6 Pages.

Mulholland, R.S., Synergistic Multi-polar Radiofrequency and Pulsed Magnetic Fields in the Non-Invasive Treatment of Skin Laxity and Body Contouring, 4 pages.

Neuro Star, TMS Therapy, Bringing Hope to Patients with Depression, 2013, 6 Pages.

Neurosoft, Ivanovo, Since 1992, Magnetic Stimulator, Neuro-MS, Technical Manual, Neurosoft Ltd, Ivanovo, Russia, 2006, 67 Pages.

Nexstim NBS System, Navigated Brain Stimulation, Noninvasive, direct cortical mapping, 2012, 5 Pages.

Obsluze, N.K.,Usage Instructions, User's Manual, Device for high-induction magnetic stimulation of type designation:Saluter Moti, 2016, 88 Pages.

Operating Manual: Magstim D70$^2$ Coil, MOP06-EN, Revision 01, The Magstim Company Limited, Feb. 2012, 14 Pages.

Operating Manual: Magstim Magstim 200$^2$, MOP01-EN, Revision 01, The Magstim Company Limited, Sep. 2011, 25 Pages.

Operating Manual: Magstim, Magstim Alpha Coil Range, MOP11-EN, Revision 01, Oct. 2012, 18 Pages.

Operating Manual: Magstim, Magstim Bistim$^2$, MOP02-EN, Revision, The Magstim Company Limited, 01, Sep. 2011, 27 Pages.

Operating Manual, Magstim, Model 200, P/N 3001-01, Double 70mm, Remote Coil, P/N 3190-00, The Magstim Company Limited, 2006, 32 pages.

Operating Manual: Magstim R, 2nd, Generation Coil Family, 3100-23-02, Magstim Coils, The Magstim Company Limited, Nov. 2002, 14 Pages.

Operating Manual, Magstim R Air-Cooled Double 70mm Coil System, 1600-23-04, The Magstim Company Limited, 1999, 18 Pages.

Operating Manual: Magstim R, Bistim System, P/N 3234-23-01, The Magstim Company Limited, Nov. 2004, 30 Pages.

Operating Manual: Magstim R, Coils & Accessories, 1623-23-07, Magstim Coils & Accessories, May 2010, 24 Pages.

Operating Manual: Magstim, RAPID2, P/N 3576-23-09, The Magstim Company Ltd, Nov. 2009, 61 Pages.

Operator's Manual: BTL Emsculpt, BTL Industries Ltd, United Kingdom, 2018, 35 pages.

Operator's Manual: BTL, HPM-6000U, BTL Industries Ltd, United Kingdom, Dec. 2016, 36 pages.

Papimi, For Scientific Research, Pap Ion Magnetic Inductor, Presentation, Magnetotherapeutic Device, Nov. 2009, 61 Pages.

Podebradsky.K., et al., Clinical study of high-inductive electromagnetic stimulator SALUS talent, 2010, 8 pages.

Polkey M.I., et al., "Functional Magnetic Stimulation of the Abdominal Muscles in Humans," American Journal of Respiratory and Critical Care Medicine, 160(2):513-522, American Thoracic Society, United States (Aug. 1999).

Polkey, M.I., et al., "Quadriceps Strength and Fatigue Assessed by Magnetic Stimulation of the Femoral Nerve in Man," Muscle Nerve, 19(5):549-555, John Wiley & Sons, United States, (May 1996).

Quick Start Manuals, Magstim Super Rapid Plus Quick Start, Aalto TMS Laboratory, Aalto School of Science, 2013, 7 Pages.

Salus Talent, a Vertice and Talos, Drott, 6 pages.

Salus Talent, Deep Penetrating Electro-Magnetic Stimulator, CR Technology, 4 pages.

Salus Talent, Deep Penetrating Electro-Magnetic Stimulator, Rehabilitation Medical Company, New choice, new satisfaction, Talent, 4 pages.

Salus Talent, Electro Magnetic Stimulator, CR Technology, 9 Pages.

Salus Talent Pro, Specification, 2 pages.

Salus, Talent Pro, The Birth of Salus Talent Pro inspired by 10 Years of Experience, Specification, Rehabilitation Medical Company, Slimon, 2 pages.

Salus, Talent Pro, The World's 1st Development 3 Tesla, 2Channel Magnetic field Therapy, Slimon, 10 pages.

Salus Talent-A, Remed, User Guide, High Intensity Electro Magnetic Field Therapy, 2017, 37 pages.

Salus-Talent, Device for Deep Electromagnetic Stimulation, Nowosc, Fizjoterapia, 6 Pages.

DuoMAG Magnetic Stimulator, Alien Technik User Manuel, Jun. 26, 2012, 48 pages, Version 2.1.

Szecsi, J., et al., "A Comparison of Functional Electrical and Magnetic Stimulation for Propelled Cycling of Paretic Patients," Archives of Physical Medicine and Rehabilitation, 90(4):564-570, W.B. Saunders, United States, (Apr. 2009).

Szecsi, J., et al., "Force-pain Relationship in Functional Magnetic and Electrical Stimulation of Subjects With Paresis and Preserved Sensation," Clinical Neurophysiology, 121(9):1589-1597, Elsevier, Netherlands, (Sep. 2010).

Taylor, J.L, "Magnetic Muscle Stimulation Produces Fatigue Without Effort," Journal of Applied Physiology (1985), 103(3):733-734, American Physiological Society, United States, (Sep. 2007).

Tesla Stym, Iskra Medical, Tone the inner muscle with FMS Functional Magnetic Stimulation, 2013, 4 pages.

Uro Diagnostic Clinic, Now in UDC, Automated pelvic floor muscle training, QRS International AG, 16 Pages.

User Guide: Mag Venture, Magpro family, MagPro R30, MagPro R30 with MagOption, MagPro X100, MagPro X100 with MagOption, MagPro software v.5.0, US-edition, MagPro family User Guide, 2010, 52 Pages.

User Guide, Salus Talent Pro, REMED, High Intensity Electro magnetic Field Therapy -2 Channel, 2017, Version M-1.0.0, 45 pages.

User Guide, Salus Talent, REMED, High Intensity Electro magnetic Field Therapy, Version. M-1.0.0, 2017, 40 pages.

User's Manual: BTL-6000, Super Inductive System Elite, BBTL Industries Ltd, United Kingdom, Sep. 2016, 36 pages.

(56) References Cited

OTHER PUBLICATIONS

User Manual: Electro-magnetic Stimulator, Salus-Talent, Version 1.00, Rehabilitation Medical Company, 2013, 34 Pages.
User Manual: Regenetron Pro, System Information, Regenetron Pro User Manual, Nov. 2014, 7 Pages.
Verges S., et al., "Comparison of Electrical and Magnetic Stimulations to Assess Quadriceps Muscle Function," Journal of Applied Physiology (1985), 106(2):701-710, American Physiological Society, United States, (Feb. 2009).
Wasilewski, M.L., Academy of Aesthetic and Anti-Aging Medicine, Application of magnetic fields with deep stimulation in the fight against local obesity of lower limbs, BTL, 2012, 4 pages.
MAG Expert, 2 pages.
Salus Talent—Pop Double, 1 page.

\* cited by examiner

DEVICE FOR REPETITIVE NERVE STIMULATION IN ORDER TO BREAK DOWN FAT TISSUE MEANS OF INDUCTIVE MAGNETIC FIELDS

CROSS REFERENCE TO RELATED APPLICATION

This application is related to and claims priority from the German PCT Patent Application No. PCT/IB2013/001896 filed on Jul. 2, 2013, which claims priority to German Patent Application No. 10 2012 013 534.3 filed on Jul. 5, 2012.

The present invention makes use of the effect of stimulating muscle contractions by contactless induction of electrical fields by means of pulse-shaped magnetic fields in the tissue. Pulsating magnetic fields are also capable of exciting ion transport by influencing the electric currents and measurably increasing metabolism. There is a demonstrable increase in blood circulation and an increased supply of oxygen. These effects are currently being medically evaluated from the point of view of the reactivation of muscles after illness or accident and have already led to corresponding inventions. Thus, from DE 10 2007 044 445 A1, a training device with magnetic stimulation is known wherein in conjunction with means for mechanically guiding an intended movement of a joint in a paralysed body part, this body part is stimulated to move. From US 2005/203332 A1, a device for the treatment of osteoporosis and other musculo-skeletal diseases is known in which the patient, lying on a couch, is surrounded at the respective part of the body by a cylindrical coil which generates an electromagnetic field. From U.S. Pat. No. 6,213,933 B1 a device and a method for dissolving blood clots in human body parts can be inferred, in which the patient lies on an elongated platform over which a transversely extending, longitudinally movable holder with a water-cooled magnetic field coil of the butterfly type is arranged for stimulation. In order to position the magnetic field coil, the holder is simply pushed over the part of the body that is to be treated. The frequency and duration of stimulation is controlled by an interactive programme on a PC. Another electromagnetic system known from US 2003/0158585 A1 uses ergonomic stimulating coils in the form of flexible flat or cylindrical coils, adapted to the contour of the particular body part, for therapeutic treatment, for stimulating nerves, muscles and other tissues of the human body.

Beyond this—and not previously utilised—muscle excitation by magnetic field stimulation leads to a breakdown of fatty tissue in the area around the muscles, as the Applicant has demonstrated by numerous experiments, particularly on obese and muscular test subjects. In slender test subjects, there is a development of muscle with no significant weight loss.

Admittedly, there were already devices and methods for treating obesity or excess weight by means of pulsating magnetic fields, but these either require, in addition to the field-generating coil, another permanent magnet in contact with the surface of the body (DE 100 62 050 A1) or they act indirectly through a magnetic field that activates the thyroid (DE 10 2009 043 728 A1) and also have to be applied to the body by means of a neck band.

Thus, using the experience and findings described above, the object of the invention is to provide a device and a method for repetitive nerve stimulation for breaking down fatty tissue by means of inductive magnetic fields, which permit easy patient-centred adjustment and control, in order to reduce fatty tissue in defined regions of the body, such as the abdomen, buttocks or thighs, in targeted manner and without any body contact.

This object is achieved by the device claimed in claim 1 and the method claimed in claim 14. Advantageous embodiments of the invention are the subject of the sub-claims.

Advantages of the invention consist particularly in the contactless induction of excitation, the associated low levels of the pain stimulation that occurs with alternative electrical excitation, the large area of excitation and the ability to position the stimulation-producing coil to suit the individual body shape of the patient.

Essential components of the device are a large-area magnetic field coil through which current passes, hereinafter referred to as the stimulation coil, which is attached to a stand. Different coil shapes are provided for the treatment of the abdomen, buttocks and thighs.

The stimulation coil produces magnetic fields with peaks at a magnetic flow density of 0.01 T to 0.1 T at about 5 cm in front of the surface of the coil. The magnetic field can be varied over time and consists of diphase or monophase pulses with a pulse duration T of 100 μs to 300 μs. The repeat frequency of the pulses (stimulation frequency $f_p$) is 10 Hz to 30 Hz. Maximum electric field intensities of 0.1 V/cm to 1 V/cm are achieved by induction at the stimulation site in the tissue. The magnetic field of the coil is approximately locally constant in magnitude throughout the volume of tissue to be treated. Parameters of a typical coil are shown in Table 1.

TABLE 1

Overview of the parameters of the coil for the abdominal area

| Variable | Value |
|---|---|
| Length of conductor | 200 cm |
| Cross-sectional area | 1 cm$^2$ |
| Distance between adjacent coil conductors | 1 cm |
| Maximum current amplitude I | 1000 A |
| Max. magn. flow density B, 5 cm in front of the coil surface | 0.01 T |
| Induced electrical field intensity (maximum), E | 0.1 V cm$^{-1}$ |
| Forces between adjacent coil conductors | 0.2 Ncm$^{-1}$ |
| Inductivity of the coil, L | 15 10$^{-6}$ H |
| Pulse frequency, f | 5 10$^3$ Hz |
| Inductive resistance $Z_L$ at f | 470 m Ohm |
| Inductive voltage drop at I | 470 V |
| Ohmic resistance, R | 36 m Ohm |
| Stimulation frequency, $f_{stim}$ | 30 Hz |
| Joule's power loss, P | 120 W |

The stimulation coil is actuated by means of a pulse generator (stimulator), which is installed separately from the stand. A stimulator of the kind currently used as a prototype in medical research (IMETUM, Central Institute for Medical Technology, Technical University of Munich, Concluding Report: "Functional peripheral magnetic stimulation of motor functions in patients with central paresis, particularly hemiplegic paralysis", 2011) with a pulse length of 160 μs (diphase) may be used. The capacity of a capacitor is matched to the inductivity of the stimulation coil in order to tune the resonating frequency of an LC resonator consisting of the stimulation coil and the capacitor, to the frequency corresponding to the pulse duration. The electric fields required give rise to high currents through the coil in the range from 500 A to 6000 A.

The large area of the coil enables it to have an open, non-cast structure. As a result, the considerable Joule's heat produced in the coil can be removed by means of an air fan.

Airflow is provided for effective cooling. Contamination and dust turbulence are prevented by filter mats.

The treatment times range from 1 min to 45 min. The long times can be achieved without overheating of the coil thanks to the effective cooling and the coil design.

The coil itself may, on account of its size, be produced as a self-supporting structure of solid metal (e.g. copper or aluminium). This assists the conduction of heat away from the coil conductor to its surface. The cross-section of the conductor is 1 cm$^2$ to about 2 cm$^2$. This large cross-section of the coil conductor, by comparison with that of coils used in site-selective magnetic field stimulation (focussing), reduces the ohmic resistance, thus reducing the Joule's heat.

Alternatively, the coil may also be produced from high-frequency wires, by conventional technology, to avoid skin and proximity effects. However, an estimation of the skin depth shows that this is not necessary with a pulse duration of about 200 μs.

In a solid construction, it may also be conceivable to use hollow conductors which are cooled by a coolant liquid.

The stimulation coil is encapsulated in a plastic housing. The housing ensures protection from contact voltage and at the same time directs the coolant air.

The fan produces a current of coolant air which reaches the coil through air inlet openings and air guiding elements fitted with filters which are provided in the plastic housing of the stimulation coil, and this coolant air is supplied to the air outlet openings of the fan through an air guide made of plastics which is arranged around the electric connecting leads to the coil. The fan may consequently be arranged at the back of the stand and outside the magnetic field of the stimulation coil, thus preventing any adverse effects on the electric fan motor.

As a result of the high currents, high mechanical forces occur between the conductor sections of the stimulation coil and the connecting leads. These are absorbed by ceramic retaining elements which maintain a spacing.

The electric connecting wires to the stimulation coil in the stand are of solid construction with no movable cables. This permits an optimum release of heat into the air, absorption of the magnetic forces and high operational reliability.

The stimulation coil is mounted on a holder which is formed by the solid current supply lines themselves. This holder positions the coil at an adequate distance from the stand; the unwanted eddy currents induced in the stand by the coil are minimised in this way.

A stimulation coil can easily be changed after opening a torsionally and axially mounted closure sleeve with a bayonet closure and loosening two screws for the connecting leads. This is significant, as different optimum coil shapes with different housings are used for different areas of the body (abdomen, thighs and buttocks).

The positioning of the stimulation coil relative to the patient can be varied by means of a variable-height pedestal. Thus the connecting leads to the stimulation coil can be made rigid in design and changes in the inductivity and input resistance caused by changes of position can be avoided.

Alternatively, positioning of the stimulation coil on the stand could be carried out by the use of clamping closures in vertical rails.

The stimulation of muscle contraction can be optimised by means of a feedback link. For this purpose, the contractions triggered by a stimulation coil are observed using a camera integrated into the stand and corresponding signals are transmitted to a computer (e.g. a laptop). This controls the electrical pulses located at the output of the pulse generator in terms of pulse form, duration, amplitude and treatment time, by means of a corresponding programme, depending on the signals received.

An embodiment of the invention which demonstrates further advantages and special features is shown in FIGS. 1 to 8 and described in more detail hereinafter.

Figure 1:
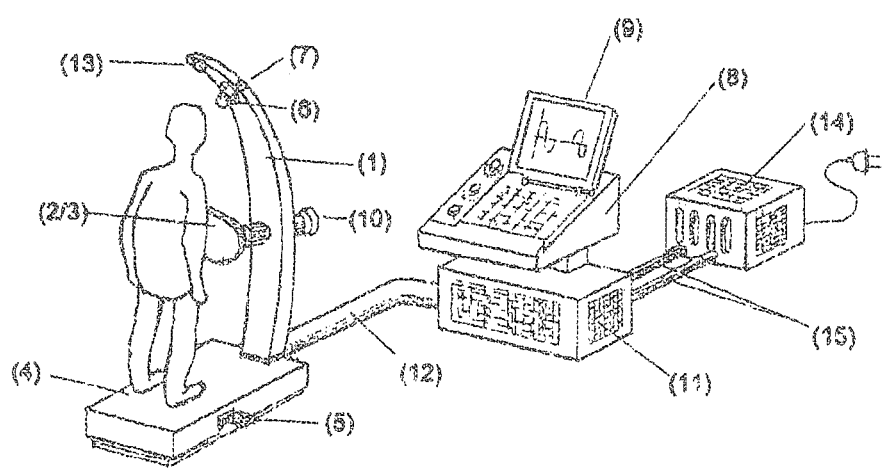
FIG. 1 is an overall view of the device for repetitive nerve stimulation for breaking down fatty issue by means of inductive magnetic fields.

FIG. 1 shows, in overall view, the device as claimed for repetitive nerve stimulation for breaking down fatty tissue by means of inductive magnetic fields, having a stimulation coil (3) replaceably attached to a stand (1) and accommodated in a plastic housing (2), a variable-height pedestal (4) with a foot pump (5) for adjustable positioning to tailor it individually to a patient's body, a pivotable camera (6) integrated in the stand (1) with an adjustment ring (7), for observing the muscle contractions triggered and for feeding back to a laptop (9) integrated in an operating console (8), said laptop comprising control software for computer-aided optimisation of the stimulation, a fan (10) for cooling the magnetic field coil (3), a pulse generator (11) for electrically actuating the magnetic field coil (3), a shielded cable channel (12) for the necessary electrical connecting wires between the stand (1) and the pulse generator (11) or the operating console (8) and a spotlight (13) for correctly illuminating the area of the body captured by the camera (6). It should be mentioned that the pulse generator (11) may advantageously be arranged directly on the stand (1) in order to minimise conduction losses. In this case, therefore, the cable channel (12) shown is dispensed with. Also shown is the power unit (14) belonging to the voltage supply of the device, which is configured and installed separately on account of the high heat levels produced, with output voltages of between 500 and 1000 V and the associated connecting cables (15).

Figure 2:
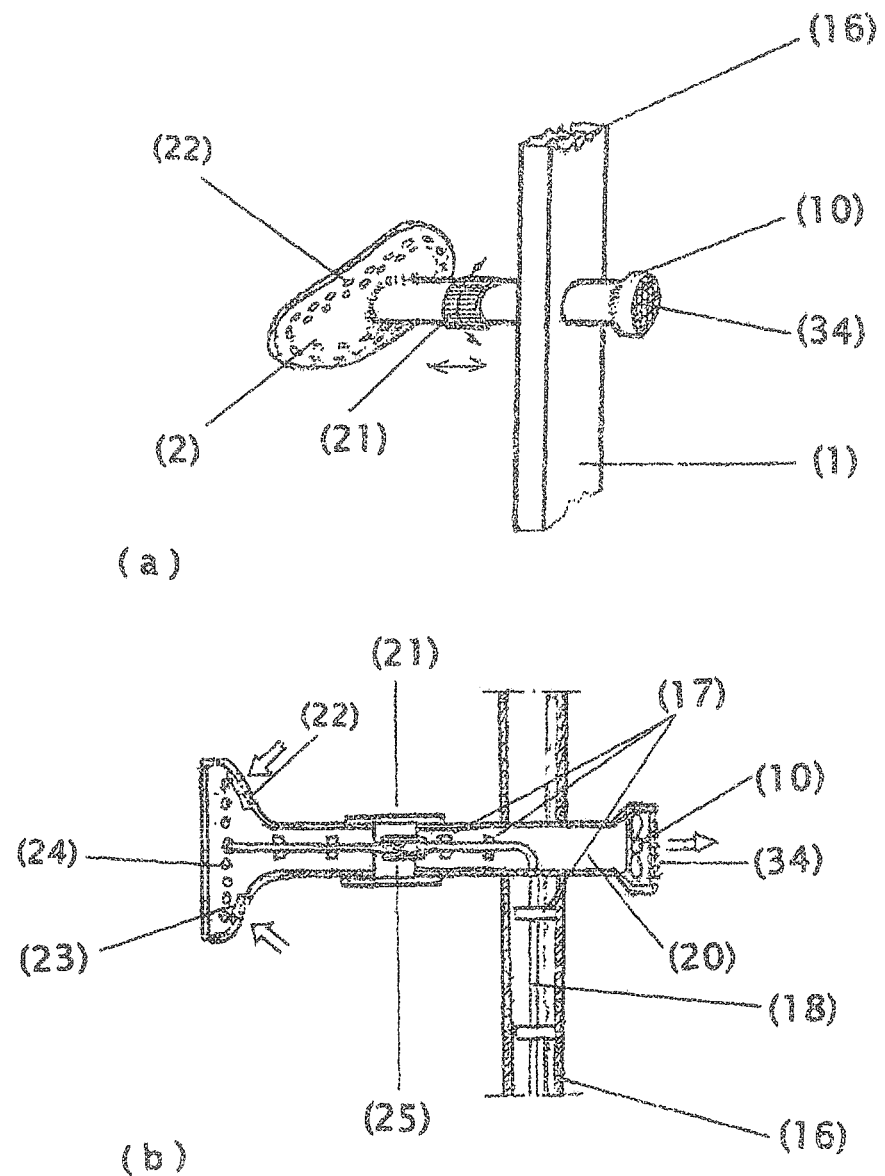
FIG. 2 is a detailed view of the stand/stimulation coil connecting arrangement in
  (a) perspective view and
  (b) sectional view.

The stand (12) approximately adapted to the magnetic field line pattern in the upper region consists essentially of a hollow frame (16) made of plastics with internally located ceramic retaining elements (17) for the precise positioning of the spaced-apart connecting leads (18, 19) with a lead cross-section of 1.5 cm² (FIG. 2a, b). These connecting leads (18, 19) ensure the passage of current between the pulse generator (11) and the stimulation coil (3). They may also be embodied as hollow conductors. Roughly level with a patient's waist, the stand (1) comprises a fixedly installed tubular air conveying channel (20) extending horizontally and transversely through the stand (1), with the connecting leads (18, 19) inside it. The connecting leads (18, 19) are passed from the air conveying channel (20) through sealed bores into the stand (1).

FIG. 1 further shows the camera (6) also provided in the stand (1), which can be positioned by means of an adjustment ring (7) so that the part of the body being treated is reliably captured. A spotlight (13) at the upper end of the stand (1) serves to illuminate the part of the body being treated.

The variable-height pedestal (4) may comprise a mechanical lifting device which is operated and locked by means of a foot lever (5). A vertical upright is a possibility. Scissor-type supports arranged vertically above one another with a threaded spindle interposed horizontally may also be opened or closed for the height adjustment, the threaded spindle being rotated by hand or by an electric motor. A hydraulic lifting cylinder with a foot pump may be used as another means of adjusting the height of the pedestal (4).

FIG. 2a shows the stand/stimulation coil connecting arrangement in detail, comprising the stand (1), the air conveying channel (20) and the fan (10) for cooling the connecting leads (18, 19) and the stimulation coil (3). A closure sleeve (21) with bayonet closure, mounted to be axially movable and rotatable, covers the start of the air conveying channel (20) and the end of the stimulation coil (3) to prevent touching of the lead couplings.

FIG. 2b is a sectional view of the stand/stimulation coil connecting arrangement. The air conveying channel (20) in the hollow frame (16) of the stand (1) comprises, at an end remote from the patient, the fan (10) with air outlet openings (34) which aspirates air through the air inlet openings (22) in the plastic housing (2) of the stimulation coil (3), through filter mats (23), past air guidance elements (not shown), the windings (24) of the stimulation coil (3) and the connecting leads (18, 19), in order to cool it. The lead coupling (25) for the outgoing and return conductors of the connecting leads (18, 19) is also shown.

Figure 3:
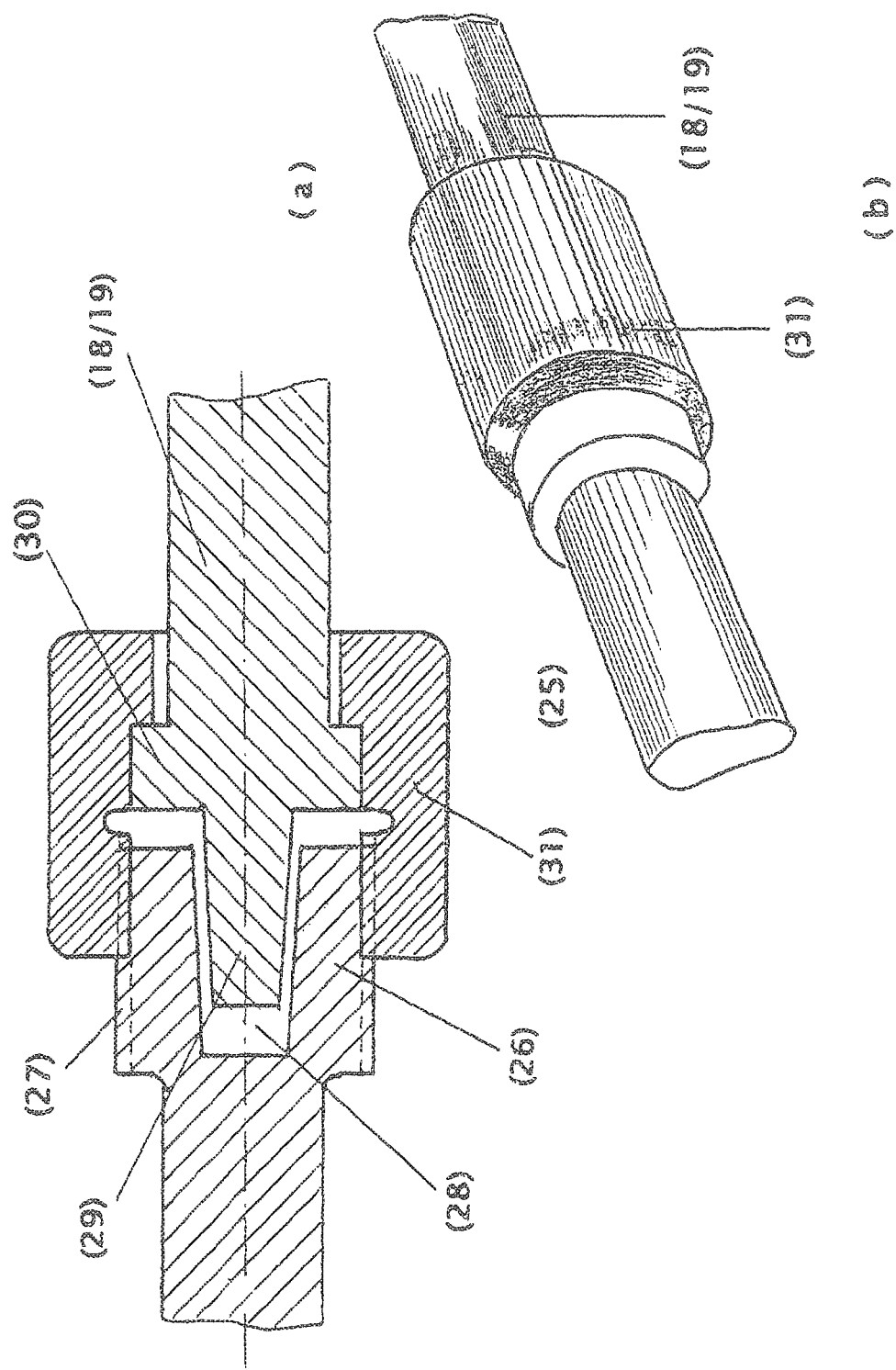
FIG. 3 shows the lead coupling for outgoing and return conductors within the stand/stimulation coil connecting arrangement in
  (a) sectional view and
  (b) perspective view in the coupled state.

FIG. 3a shows the lead coupling (25) for outgoing and return conductors in section. Each end of a conductor in the stimulation coil (3) comprises a thickened, cylindrical end portion (26) with an external thread (27). A horizontal trapezoidal slot (28) is milled into this end portion (26). A trapezoidal tab (29) protruding from a thickened, cylindrical end portion (30) of one of the connecting leads (18) or (19) engages in said slot (28). An internally threaded screw bushing (31) which surrounds one of the thickened end portions (30) of the connecting leads (18) or (19) is screwed onto the external thread (27) of one end portion (26) in each case and connects the connecting leads (18, 19) to the stimulation coil (3). By means of these two lead couplings which can be pushed on and screwed tight, the stimulation coil (3) is supported by the connecting leads (18, 19). This special screw connection simultaneously serves to conduct electricity. As the conical flanks of the trapezoidal slot (28) lie with their surface against the flanks of the trapezoidal tab (29), there is also a slight contact resistance.

FIG. 3b is a perspective view of the lead coupling used for outgoing and return conductors in the screwed state.

Figure 4:
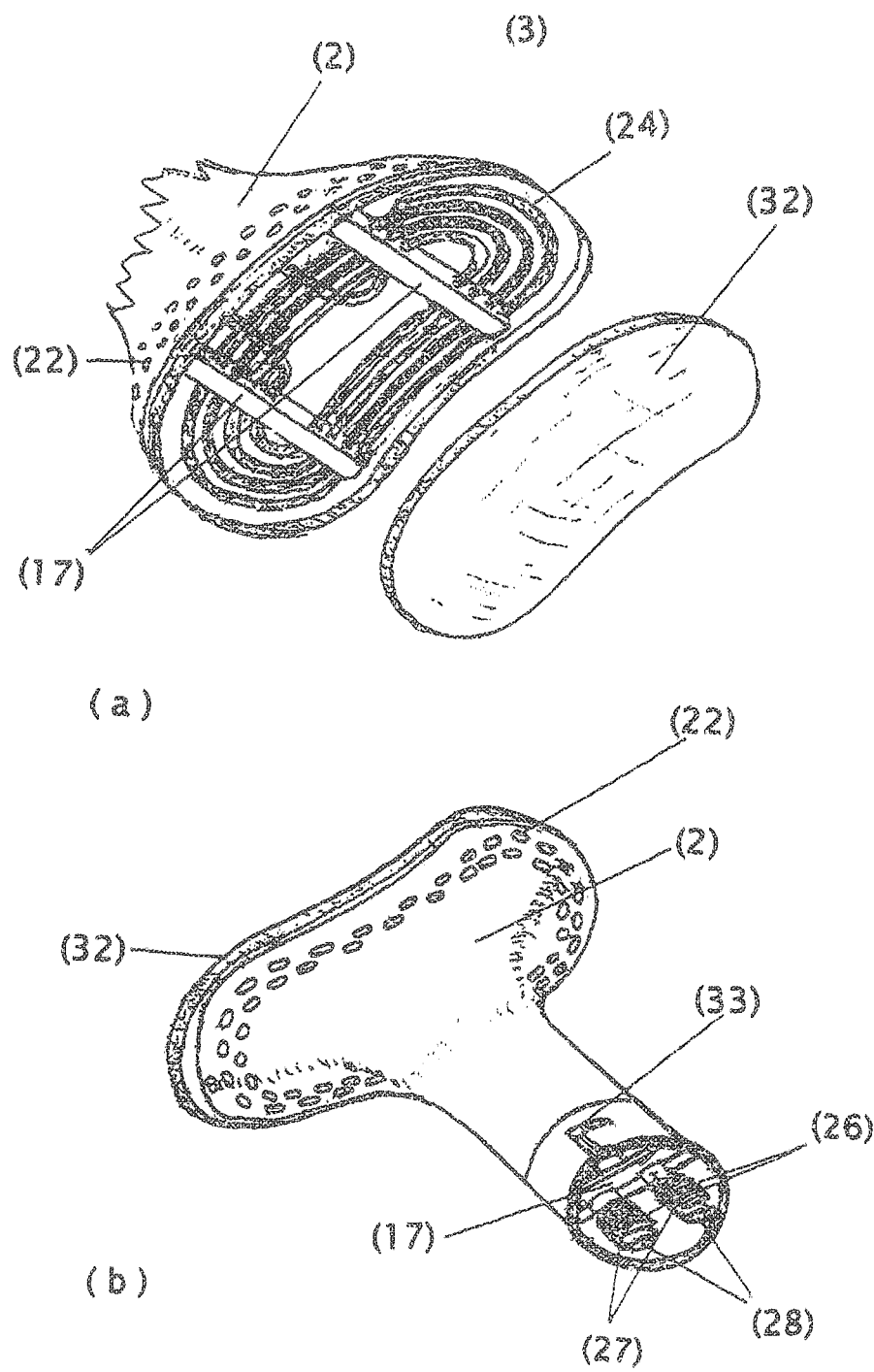
FIG. 4 shows a stimulation coil for treatment of the abdomen in
  (a) perspective view of the housing from the front (treatment side) with the protective cover open, and
  (b) perspective view of the housing from behind (stand side) with the lead couplings visible.
Figure 5:
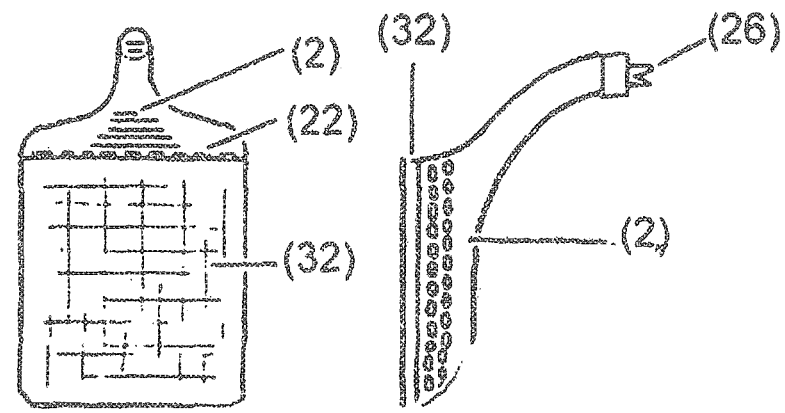
FIG. 5 shows a stimulation coil for treatment of the buttocks region in
  (a) a view of the housing from in front (treatment side)
  (b) a view of the housing from the side
  (c) a view of the housing from above
  (d) the configuration of the coil inside the housing, seen from the viewpoint of the treated person.
Figure 5:
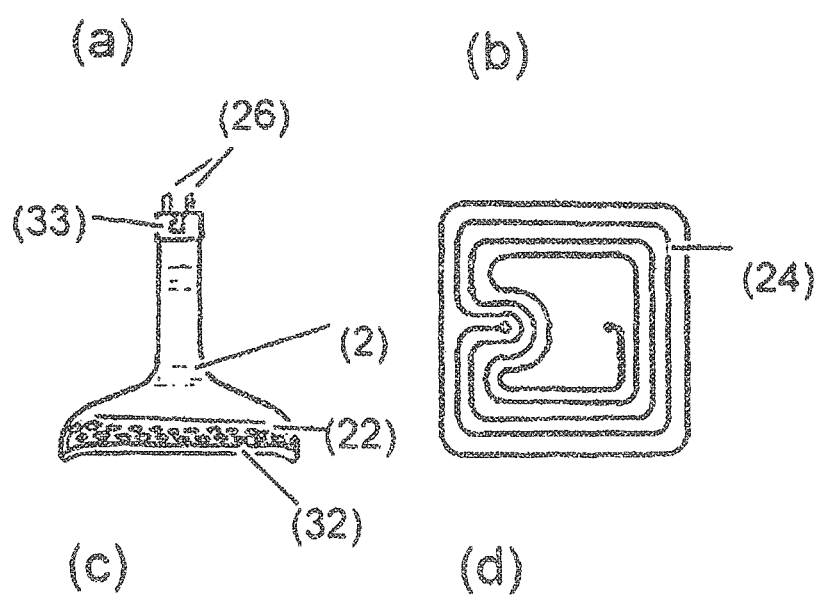
Figure 6:
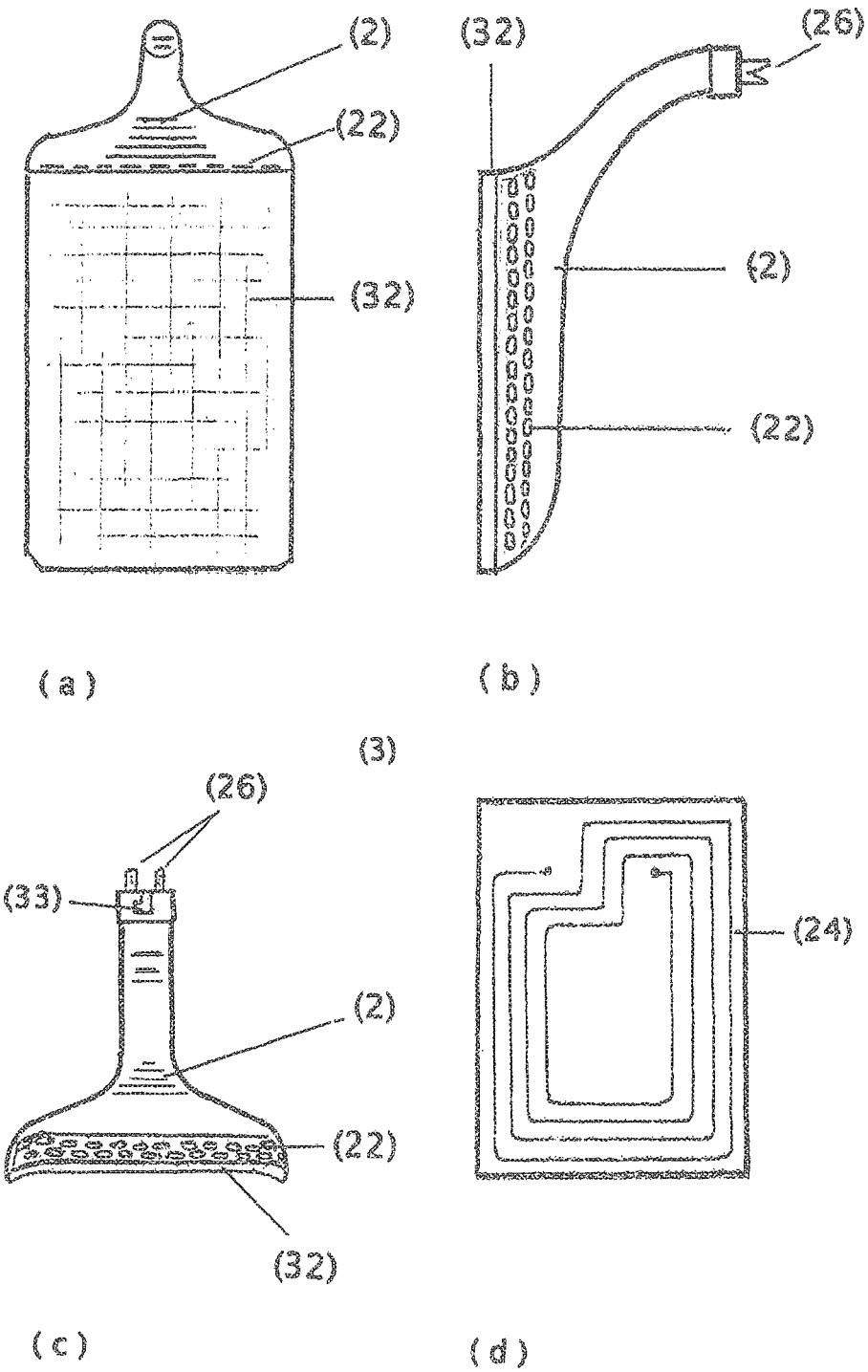
FIG. 6 shows a stimulation coil for treatment of the thighs in
  (a) a view of the housing from in front (treatment side)
  (b) a view of the housing from the side
  (c) a view of the housing from above
  (d) the configuration of the coil inside the housing, seen from the viewpoint of the treated person.

FIG. 4a shows, for example, the stimulation coil (3) for treating the abdomen, in perspective view from the front (treatment side). The drawing shows a clampable protective cover (32) which has been removed, and a substantially trumpet-shaped plastic housing (2). On the inside of this trumpet-shaped plastic housing (2) are a plurality of ceramic retaining elements (17) for accommodating the windings (24) of the stimulation coil (3). The ends of the windings (24) of the stimulation coil (3) are guided parallel to the thickened end portions (26). The windings (24) for treatment of the abdomen themselves run substantially in an oval and cover an area of about 20 cm×30 cm. The air inlet openings (22) can also be seen.

FIG. 4b shows the stimulation coil (3) for treatment of the abdomen, in perspective view from behind (the stand side). Clearly visible are the thickened end portions (26) with the external threads (27), the respective trapezoidal slots (28), ceramic retaining elements (17) and a groove (33) in the plastic housing (2) of the stimulation coil (3) for guiding the axial and rotary movement of the closure sleeve (21).

FIGS. 5a, 5b, 5c and 5d show various representations of a stimulation coil (3) for treating the buttocks region; (a) the housing viewed from in front, (b) the housing viewed from the side, (c) the housing viewed from above and (d) the configuration of the coil inside the housing, seen from the viewpoint of the person being treated. This stimulation coil (3) has the same internal construction as the stimulation coil (3) for treating the abdomen and essentially only differs in the external shape of the housing. The treatment side of the housing has a rounded-off square shape measuring about 15 cm×15 cm. The protective cover (32) has a slightly concave curvature. The stimulation coil (3) itself comprises suitably shaped windings (24) extending in a square configuration. The back of the plastic housing (2) has a swan-necked shape so that the stimulation coil (3) can act slightly below the patient's waist.

FIGS. 6a, 6b, 6c and 6d show various representations of a stimulation coil (3) for treating the thighs; (a) the housing viewed from in front, (b) the housing viewed from the side, (c) the housing viewed from above and (d) the configuration of the coil inside the housing, seen from the viewpoint of the person being treated. This stimulation coil (3) has the same basic construction as the stimulation coil (3) for treating the buttocks, the difference being that the treatment side has a rounded-off rectangular shape measuring about 10 cm×20 cm, the protective cover having a slightly concave curvature extending in the vertical direction.

Figure 7:
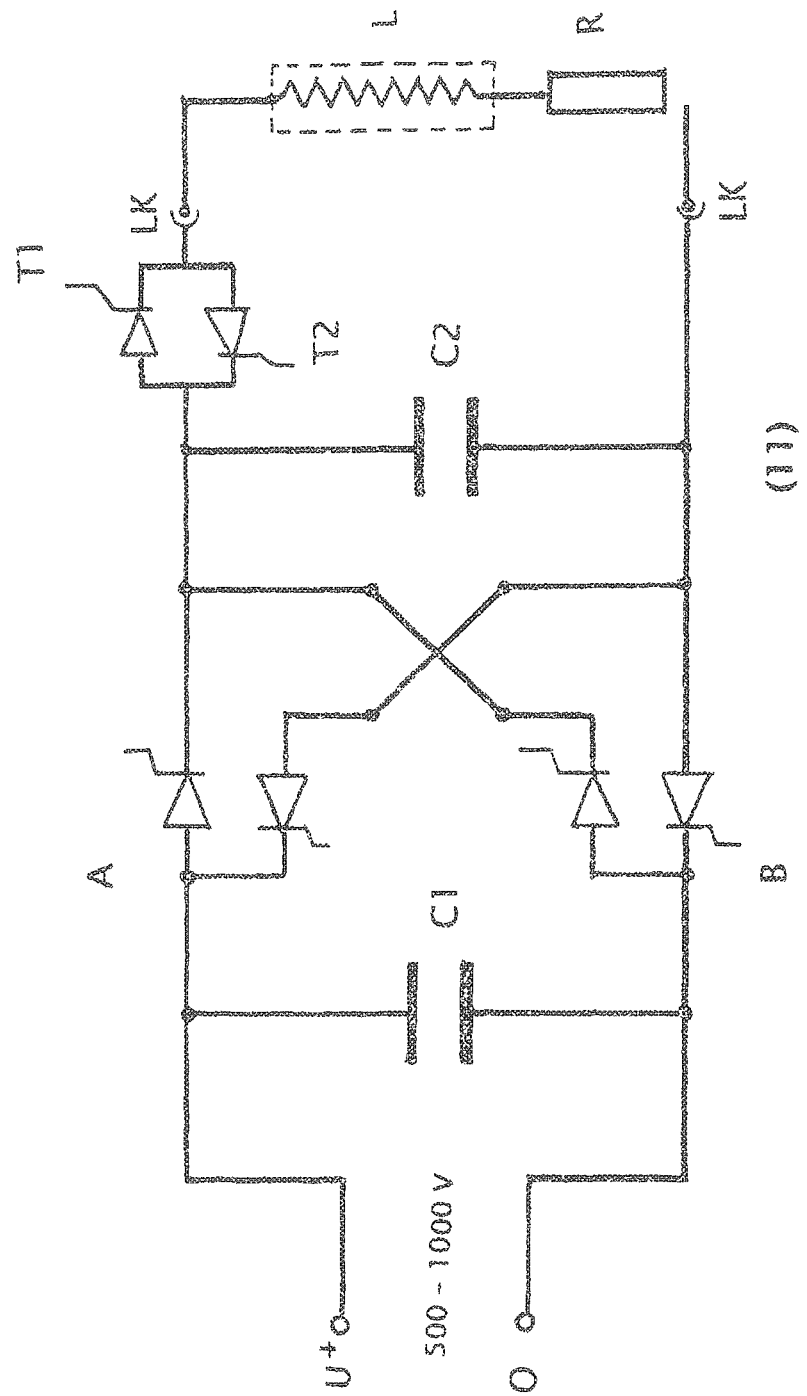
FIG. 7 is a basic circuit diagram of a bipolar pulse generator.
Figure 8:
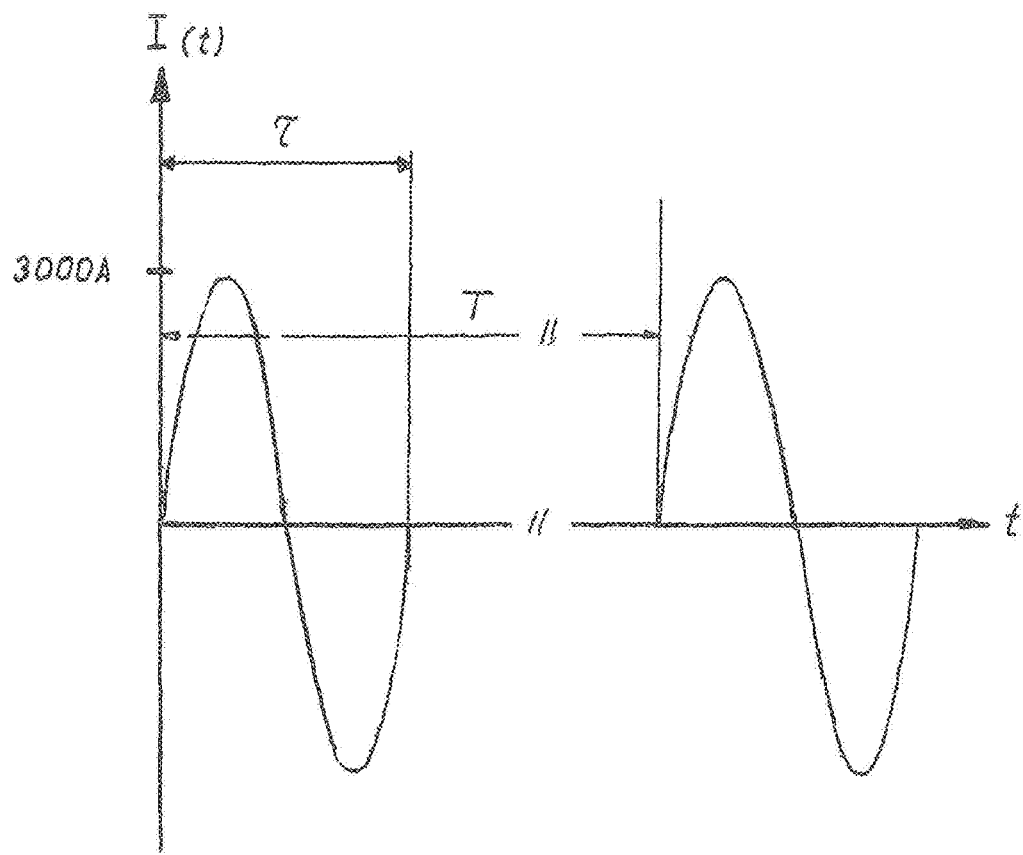
FIG. 8 shows an idealised current flow in a stimulation coil with bipolar actuation by the pulse generator.

FIG. 7 shows, by way of example, a basic circuit diagram of a conventional pulse generator (11) as used here, which only generates its own stimulation pulse producing unit in conjunction with the stimulation coil (L) (cf. lead couplings LK). Voltages of between 500 V and 1000 V coming from the separate power unit (14) are selected in stages of 50 V by means of electronic switches (not shown here) which are controlled either manually by means of the operating console (8) or by the computer (9), and applied to the reservoir capacitor (C1) at the input of the pulse generator (11), for storage. The selected charge voltage of this reservoir capacitor (C1) essentially determines the stimulation power and hence the amplitude level of the stimulation pulse that is to be generated. The actual energy store, the pulse capacitor (C2), is charged up and recharged by means of the thyristor circuits A and B. In principle the pulse capacitor (C2) forms with the stimulation coil (L) an oscillating circuit which is damped by the ohmic resistors of the connecting leads and couplings, generally shown in the drawing as ohmic resistor (R). Repetitive discharges of the pulse capacitor (C2) and hence the stimulation frequency $f_{stim}$ are controlled by means of two thyristors (T1, T2) connected in antiparallel manner and capable of carrying heavy current, which connect the pulse capacitor (C2) to the stimulation coil (L). As a result of the antiparallel connection of the thyristors (T1, T2), sinusoidal diphase voltage and current pulses may be generated (FIG. 8 and associated description). Their pulse duration T can be adjusted by the connection or disconnection of capacitors (not shown here) connected in parallel to the pulse capacitor (C2), as this enables the overall capacity in the oscillating circuit and hence the oscillating circuit frequency $f_p$ ($f_p=1/(2\pi\sqrt{LC})$) to be varied. Both the thyristor actuation for selecting the stimulation frequency $f_{stim}$ and also the number of parallel-connected capacitors for determining the pulse duration T can be manually pre-set on the operating console (11) or are controlled by the computer (9).

FIG. 8 shows, by way of example, an idealised current flow in a stimulation coil (3) with diphase actuation by the pulse generator (11). A stimulation coil inductivity of $15\times10^{-6}$ H, a charging voltage $U_{C2}$ of 1000 V and a diphase stimulation pulse with a pulse duration T of 300 µs were assumed. After the thyristor (T1) is switched through (FIG. 7) a positive half-wave of a sinusoidal current flow with a maximum amplitude of about 3000 A is obtained. At time T/2, i.e. after half the pulse duration T has ended, the current I(t) in the oscillation circuit changes its polarity and the thyristor (T2) (FIG. 7) is switched through and takes over the current conduction until a complete sinusoidal oscillation has been reached. Meanwhile, the thyristor (T1) is blocked. The negative half-wave of the sinusoidal current flow thus produced also has a maximum amplitude of about 3000 A. As both thyristors (T1, T2) are blocked after a pulse duration T, further oscillation is prevented, so that only a diphase pulse is produced. Only after a stimulation pulse repeat time T has been reached which corresponds to the reciprocal of the stimulation frequency $f_{stim}$, are the thyristors (T1, T2) switched through again in the manner described and the pulse-shaped current flow in the stimulation coil is obtained once more, as also shown in FIG. 8. The pulse-shaped currents shown then ensure, in the stimulation coil (3), a corresponding formation and breakdown of pulse-shaped magnetic alternating fields within a treatment time interval that can be set at the operating console (8) or is controlled by the computer (9).

If the thyristor T2 is never switched through, a monophase current pulse is produced which consists only of the positive half-wave of the sinusoidal current flow I(t) shown in FIG. 8.

LIST OF REFERENCE NUMERALS 1 stand
2 plastic housing
3 magnetic field coil/stimulation coil
4 pedestal
5 foot lever
6 camera
7 adjustment ring
8 operating console
9 laptop
10 fan
11 pulse generator
12 cable channel
13 spotlight
14 power device
15 connecting cable
16 hollow frame
17 retaining element
18 connecting lead
19 connecting lead
20 air conveying channel
21 closure sleeve
22 air inlet openings
23 filter mats
24 windings
25 lead coupling
26 end portion
27 external thread
28 slot
29 tab
30 end portion
31 screw bushing
32 protective cover
33 groove
34 air outlet opening

What is claimed is:

1. A method for breaking down fatty tissue of a patient using a device including a power unit, at least one switch, a pulse capacitor and a stimulation coil, the method comprising:
    placing the stimulation coil in a plastic housing proximate to the patient wherein the stimulation coil is not in contact with the patient;
    charging the pulse capacitor;
    switching the at least one switch in order to enable providing a current in a range of 500 A to 6000 A to the stimulation coil and generating a pulsed magnetic field with the stimulation coil;
    applying diphasic pulses of the magnetic field to a muscle of the patient within a body region including at least one of the thighs, buttocks, abdomen, or waist in order to cause a repetitive contraction of the muscle in order to break down fatty tissue; and
    cooling the stimulation coil with a fluid cooling media, wherein the magnetic field has a magnet flux density in a range of 0.01 Tesla to 0.1 Tesla at 5 cm in front of a surface of the stimulation coil.

2. The method of claim 1, wherein the plastic housing comprises a concave curvature.

3. The method of claim 1, wherein the stimulation coil is spaced apart from the plastic housing in order to enable flowing the fluid cooling media between the stimulation coil and the plastic housing.

4. The method of claim 1, further comprising applying the pulses of the pulsed magnetic field with a stimulation frequency in a range of 10 Hz to 30 Hz.

5. The method of claim 4, wherein the stimulation coil includes a high-frequency wire.

6. The method of claim 1, wherein the pulsed magnetic field is sinusoidal.

7. A device for breaking down fatty tissue of a patient using a time-varying magnetic field, comprising:
    a power unit;
    a stimulation coil encapsulated in a plastic housing and operatively connected to the power unit;
    a pulse capacitor coupled to the stimulation coil; and
    at least one switch coupled to the stimulation coil and to the pulse capacitor, wherein the at least one switch is configured to enable discharging of the pulse capacitor to the stimulation coil with a current peak in a range of 500 A to 6000 A such that the stimulation coil generates a pulsed magnetic field with a magnetic flux density in a range of 0.01 Tesla to 0.1 Tesla at 5 cm away from a surface of the stimulation coil, wherein the pulsed magnetic field comprises diphasic pulses, wherein the stimulation coil is configured to be cooled with a fluid cooling media, and wherein the plastic housing is configured to be placed on the patient such that the stimulation coil is not in contact with the patient, and wherein the pulsed magnetic field is configured to be applied to a body region including at least one of the thighs, buttocks, or abdomen in order to cause a repetitive contraction of a muscle in order to break down fatty tissue.

8. The device of claim 7, further comprising:
an operating console configured to control the power unit such that a voltage on the pulse capacitor is regulated by the power unit.

9. The device of claim 7, wherein the device is configured to generate the pulsed magnetic field with a stimulation frequency in a range of 10 Hz to 30 Hz.

10. The device of claim 7, wherein the fluid cooling media is a liquid.

11. The device of claim 8, wherein the stimulation coil, including said plastic housing, is replaceable with a different stimulation coil including a different housing, and wherein the stimulation coil is mounted to the device by bayonet closure.

12. The device of claim 11, further comprising a mechanical holder, wherein the plastic housing is configured to be coupled to the patient by a mechanical holder.

13. The device of claim 7, wherein the at least one switch comprises a first switch and a second switch,
wherein the first switch is configured to be switched such that the pulse capacitor is discharged with the current peak in a range of 500 A to 6000 A to the stimulation coil and the stimulation coil generates a first phase of the time-varying magnetic field,
wherein the second switch is configured to be switched after the first phase of the time-varying magnetic field is generated such that the stimulation coil generates a second phase of the time-varying magnetic field, and
wherein the plastic housing is configured to be coupled to the patient by a mechanical holder.

14. A device for repetitive nerve stimulation for treatment of muscles of a patient using a pulsed magnetic field, comprising:
a power unit;
a stimulation coil operatively connected to the power unit and encapsulated in a plastic housing;
a pulse capacitor configured to provide current pulses with a current peak in a range of 500 A to 6000 A to the stimulation coil such that the stimulation coil generates the pulsed magnetic field, wherein the pulsed magnetic field is diphasic, and wherein the pulsed magnetic field has a magnetic flux density in a range of 0.01 Tesla to 0.1 Tesla at 5 cm away from a surface of the stimulation coil;
an operating console configured to control a frequency of the current pulses in a range of 10 Hz to 30 Hz such that the pulsed magnetic field is generated with a stimulation frequency in a range of 10 Hz to 30 Hz,
wherein pulses of the pulsed magnetic field are configured to trigger contractions of muscles in buttocks of the patient,
wherein the stimulation coil is cooled, and
wherein the stimulation coil, including said plastic housing, is replaceable with a different stimulation coil including a different housing.

15. The device of claim 14, wherein the pulsed magnetic field is sinusoidal.

16. The device of claim 15, further comprising:
a retaining element configured to maintain a space between the stimulation coil and the plastic housing.

17. The device of claim 15, wherein the stimulation coil is mounted to the device by bayonet closure.

18. The device of claim 15, wherein the pulsed magnetic field is able to induce an electric field having an intensity in the range of 0.1 V/cm to 1 V/cm in the patient.

19. The device of claim 15, wherein the operating console is further configured to set a pulse duration.

20. The device of claim 15, wherein the plastic housing comprises a concave curvature.

21. The device of claim 15, wherein the device is configured such that the pulsed magnetic field is applied with a pulse duration in a range of 100 µs to 300 µs.

22. A device for repetitive nerve stimulation for treatment of muscles of a patient using a pulsed magnetic field, comprising:
a stimulation coil accommodated in a housing;
a pulse capacitor configured to be charged, wherein the pulse capacitor is configured to discharge current pulses with a current peak in a range of 500 A to 6000 A to the stimulation coil so that the stimulation coil generates the pulsed magnetic field with a magnetic flux density in a range of 0.01 Tesla to 0.1 Tesla at 5 cm away from a surface of the stimulation coil, wherein the pulsed magnetic field comprises sinusoidal pulses;
a retaining element configured to maintain a space between the stimulation coil and the plastic housing such that the stimulation coil does not contact the patient; and
an operating console configured to control the generation of the current pulses and to control the frequency of the current pulses, wherein the pulsed magnetic field triggers muscle contractions of a muscle in a body region of a patient, and wherein the body region comprises the abdomen or buttocks, and wherein the stimulation coil is mounted to the device by bayonet closure.

23. The device of claim 22, wherein the stimulation coil is a flat coil.

24. The device of claim 23, wherein the pulsed magnetic field is able to induce an electric field having an intensity in the range of 0.1 V/cm to 1 V/cm in the patient.

25. The device of claim 23, wherein the stimulation coil, including said plastic housing, is replaceable with a different stimulation coil including a different housing by the bayonet closure.

26. The device of claim 23, wherein the stimulation coil is configured to be cooled by a liquid.

27. The device of claim 23, wherein the plastic housing is configured to be coupled to the patient by a mechanical holder.

28. The device of claim 23, wherein the operating console is configured to control a power unit such that a voltage, when the pulsed capacitor is charged on, is regulated by the power unit.

29. The device of claim 23, wherein the pulsed magnetic field is applied with a stimulation frequency in a range of 10 Hz to 30 Hz.

* * * * *

Disclaimer

10,806,943 B2 - Tobias Sokolowski, Pullach im Isartal (DE). DEVICE FOR REPETITIVE NERVE STIMULATION IN ORDER TO BREAK DOWN FAT TISSUE MEANS OF INDUCTIVE MAGNETIC FIELDS. Patent dated October 20, 2022. Disclaimer filed June 3, 2022, by the assignee, BTL Healthcare Technologies A.S.

I hereby disclaim the following complete claims 1-29 of said patent.

*(Official Gazette, October 25, 2022)*